United States Patent [19]

O'Lenick, Jr.

[11] Patent Number: 5,428,142
[45] Date of Patent: Jun. 27, 1995

[54] SILICONE BASED GLYCOSIDES

[75] Inventor: Anthony J. O'Lenick, Jr., Lilburn, Ga.

[73] Assignee: Siltech Inc., Norcross, Ga.

[21] Appl. No.: 138,189

[22] Filed: Oct. 20, 1993

[51] Int. Cl.$^6$ .......................... C07H 1/00; C08B 37/00
[52] U.S. Cl. .................... 536/1.11; 536/120; 536/124; 536/102; 536/123.13; 536/4.1; 536/18.3; 536/18.6
[58] Field of Search ...................... 536/1.1, 17.1, 120, 536/18.5, 124, 102, 123.13

[56] References Cited

U.S. PATENT DOCUMENTS

| | | | |
|---|---|---|---|
| 4,745,186 | 5/1988 | Mudd et al. | 536/115 |
| 5,003,057 | 3/1991 | Mc Curry | 538/18.6 |
| 5,114,717 | 5/1992 | Kuznitz et al. | 424/401 |
| 5,164,492 | 11/1992 | Kitazawa et al. | 536/116 |
| 5,173,554 | 12/1992 | Kitazawa et al. | 526/238.2 |
| 5,298,240 | 3/1994 | Schroder et al. | 424/70 |

OTHER PUBLICATIONS

George Odian, Principles of Polymerization, 2nd Ed 1981 pp. 126–140.
R. Morrison and R. Boyd, Organic Chemistry, 4th Ed 1983 pp. 546–553.
Pueddemann, E. Silane Coupling Agents, 2nd Ed. 1982 pp. 35–36 and 55–57.

Primary Examiner—Michael G. Wityshyn
Assistant Examiner—Everett White

[57] ABSTRACT

The present invention relates to a series of silicone containing glycosides prepared by the reaction of a hydroxy containing dimethicone copolyol with a reducing saccharide, or a source of reducing saccharide, in the presence of a suitable catalyst. The invention also relates to the application of these novel compounds in personal care compositions for use on hair and skin.

20 Claims, No Drawings

SILICONE BASED GLYCOSIDES

BACKGROUND OF THE INVENTION

1. Field of the Invention

The present invention relates to a series of silicone containing glycosides prepared by the reaction of a hydroxy containing dimethicone copolyol with a reducing saccharide, or a source of reducing saccharide, in the presence of a suitable catalyst. The invention also relates to the application of these novel compounds in personal care compositions for use on hair and skin.

2. Related Art

The reaction of a reducing saccharide, e.g. an aldose or ketone saccharide, or a source thereof, with an alcohol results in the formation of a glycoside. Acid catalysts are used to promote the reaction between the reducing saccharide and the alcohol. When the alcohol is an alkanol, the resulting glycoside is an alkyl glycoside. Alkyl glycosides are known to those skilled in the art.

Alkyl glycosides are surface active materials which have been known for many years. They are synthesized by the reaction of a saccharide, most importantly glucose with a fatty alcohol. They have been known since the early 1900's having been described by Emil Fischer. When the sugar used is a saccharide like glucose, the resulting material is correctly called a glycoside, however when a polysaccharide is used like starch is used as a raw material, the resulting compound is more contains some alkyl glycoside and some material which more correctly is referred to as polyglycoside. Common usage however allows for either materials to be referred to as a "glycoside". The reaction of the hydroxyl group in the alcohol with the saccharide results in an ether linkage. Much work has been done recently to improve purity, color, and reduce odor and by product levels in alkyl glycosides.

U.S. Pat. No. 3,547,828 issued to Mansfield et al. discloses a process for producing alkyl glycosides which possess surface activity by reacting a saccharide with a lower alkanol (butanol) in the presence of an acid catalyst, then reacting again with a higher alkanol to produce the desired higher alkyl glycoside.

U.S. Pat. No. 5,003,057 issued to Mc Curry et al., which is incorporated herein by reference, discloses a alternate process for producing the higher alkyl surface active glycosides.

While these patents deal with interesting process modifications by which higher purity, lighter color and simpler process technology can be used to produce alkyl glycosides, none address the potential of incorporating into the molecule a silicone portion which results in unique solubility, substantivity and lower irritation properties of the glycoside class, While Mc Curry states (col 1 line 21) that these materials (alkyl glycosides) contribute surface activity, e.g. detergency, the added advantages of incorporation of silicone into the molecule has been heretofore unappreciated.

SUMMARY OF THE INVENTION

(1) Object of the Invention

It is the object of the present invention to provide a series of novel silicone containing glycoside polymers, which are substantive to skin and hair and possess outstanding emmoliency properties when applied to the skin. In addition, unlike the alkyl products heretofore known, these materials are exceptionally well tolerated by the skin and eye and are essentially non-irritating. These properties result in superior softening, conditioning and antistatic properties. Incorporation of this type of group into the silicone molecule results in increased solubility in many organic solvents. This ability to marry fatty chemistry with silicone chemistry results in unexpected solubilities and surface active properties. The compounds also contain varying amounts of ethylene oxide and propylene oxide in the molecule. This results in the ability to vary water solubility and introduce an inverse cloud point into the molecule. Inverse cloud point is well known to those skilled in the surfactant art. It is generally found in nonionic surface active agents. It is not found in quaternary compounds. The inverse cloud point is that temperature at which a soluble compound looses it's solubility in water. Inverse cloud point, also called high cloud point, is thought to be associated with the ability of the alkylene oxide chain to hydrogen bond with the water.

It is another objective of the current invention to provide silicone derived glycosides which have very low irritation values when applied to skin and eyes. Irritation is a major problem with traditional fatty glycoside materials.

Still another object of the present invention is to provide a series of glycoside silicone polymers which have differing solubilities in water and organic solvents. This is achieved by selection of the hydroxy silicone polymer used as a raw material.

Application of the compounds of the invention can be from solvent, aqueous dispersion or solution, or applied neat in these process. It is anticipated that the effective conditioning concentration of the compound of this invention ranges from 0.1% to 25% by weight.

DETAILED DESCRIPTION OF THE INVENTION

The compounds of this invention are silicone containing dimethicone copolyol glycosides made by the reaction of a dimethicone copolyol compound, a saccharide moiety or a source of a saccharide moiety, in the presence of a suitable acid catalyst. Specifically, the compounds of the present invention are silicone glycosides which are prepared by the reaction of;

(a) a dimethicone copolyol compound conforming to the following structure:

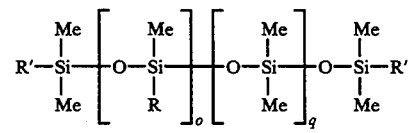

wherein:

Me is methyl;

R is —$(CH_2)_3$—O—$(EO)_a$—$(PO)_b$—$(EO)_c$—H;

R' is selected from the group consisting of $CH_3$ and —$(CH_2)_3$—O—$(EO)_a$—$(PO)_b$—$(EO)_c$—H, with the proviso that R' cannot be $CH_3$ when o is zero;

EO is —$(CH_2CH_2$—O)—;

PO is a —$(CH_2CH(CH_3)$—O)—;

a, b and c are independently integers ranging from 0 to 20;

o is an integer ranging from 0 to 200;

q is an integers ranging from 0 to 1,100;

with a saccharide or saccharide source in the presence of an acid catalyst.

It is also anticipated that the reaction may be carried out with some fatty alcohol and some dimethicone copolyol to produce a mixed product.

PREFERRED EMBODIMENTS

In a preferred embodiment a, b and c are each zero.

In another preferred embodiment a, b and c are each greater than 0.

In a preferred embodiment the saccharide is glucose.
In a preferred embodiment the saccharide is starch.
In a preferred embodiment the saccharide is fructose.
In a preferred embodiment the saccharide is sucrose.
In a preferred embodiment the saccharide is lactose.
In a preferred embodiment the saccharide is methyl glycoside.
In a preferred embodiment the saccharide is maltose.
In a preferred embodiment the saccharide is ribose.

EXAMPLES

The compounds of the present invention are prepared by the reaction of a hydroxy silicone compound and a fatty acid. Examples of suitable reactants are as follows;

Raw Materials

1. Dimethicone Copolyol Compounds

Dimethicone copolyols are known and are commercially available from Siltech Inc. Norcross Ga. They conform to the following structure:

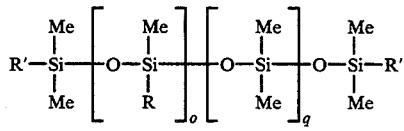

wherein:
Me is methyl;
R is —$(CH_2)_3$—O—$(EO)_a$—$(PO)_b$—$(EO)_c$—H;
R' is selected from the group consisting of $CH_3$ and —$(CH_2)_3$—O—$(EO)_a$—$(PO)_b$—$(EO)_c$—H, with the proviso that R' cannot be $CH_3$ when o is zero;
EO is —$(CH_2CH_2$—O)—;
PO is a —$(CH_2CH(CH_3)$—O)—;
a, b and c are independently integers ranging from 0 to 20;
o is an integer ranging from 0 to 200;
q is an integer ranging from 0 to 1,100.

| COMB DIMETHICONE COPOLYOLS (R' is $CH_3$) | | | | | | |
|---|---|---|---|---|---|---|
| Example | Name | a | b | c | o | q |
| 1 | Siltech H 1000 | 3 | 0 | 0 | 2 | 54 |
| 2 | Siltech H 1100 | 10 | 5 | 10 | 10 | 100 |
| 3 | Siltech H 1200 | 20 | 20 | 20 | 2 | 56 |
| 4 | Siltech H 1300 | 10 | 10 | 10 | 6 | 26 |
| 5 | Siltech H 1400 | 0 | 10 | 0 | 4 | 200 |
| 6 | Siltech H 1500 | 5 | 5 | 5 | 2 | 50 |
| 7 | Siltech H 1600 | 0 | 6 | 0 | 10 | 25 |
| 8 | Siltech H 1700 | 0 | 0 | 0 | 5 | 10 |

| TERMINAL DIMETHICONE COPOLYOLS (o is 0) | | | | | |
|---|---|---|---|---|---|
| Example | Name | a | b | c | q |
| 9 | Siltech T 710 | 0 | 0 | 0 | 11 |
| 10 | Siltech T 706 | 5 | 1 | 0 | 72 |
| 11 | Siltech T 710 | 2 | 1 | 1 | 81 |
| 12 | Siltech T 750 | 10 | 5 | 10 | 653 |
| 13 | Siltech T 790 | 20 | 20 | 20 | 1,100 |

2. Saccharides

The saccharide useful in the preparation of the compounds of the present invention are those saccharides which can be alkylated in the "1" position, commonly referred to as "reducing saccharides", or higher saccharides that can be hydrolyzed to provide such a saccharide. These saccharides are typically comprised of aldohexoses, keto-hexoses, aldo-pentoses or keto-pentoses. These materials are commercially available from several sources. Aldrich Chemical is a good source for these materials. Examples of saccharides include:

| | |
|---|---|
| Example 14 | glucose (dextrose) |
| Example 15 | fructose |
| Example 16 | mannatose |
| Example 17 | galactose |
| Example 18 | talose |
| Example 19 | allose |
| Example 20 | altrose |
| Example 21 | idose |
| Example 22 | arabinose |
| Example 23 | xylose |
| Example 24 | lyxose |
| Example 25 | ribose |

A "saccharide source" is a hydrolzable saccharides which acts as a source of reducing saccharides. These include

| | |
|---|---|
| Example 26 | starch |
| Example 27 | maltose |
| Example 28 | sucrose |
| Example 29 | lactose |
| Example 30 | maltotriose |
| Example 31 | xylobiose |
| Example 32 | mellibiose |
| Example 33 | cellobiose |
| Example 34 | raffinose |
| Example 35 | stachiose |
| Example 36 | methyl glycoside |
| Example 37 | butyl glycoside |
| Example 38 | levoglucosan |
| Example 39 | 1,6 anhydroglucofuranose. |

The physical form of the saccharide may vary. The saccharide may by liquid or solid, crystalline or amorphous, granular or powdered. Upon heating the reaction medium will become fluid and the saccharide will react. Aqueous syrups can also be utilized. The water merely evaporates off as the reaction mixture is heated.

The preferred saccharides are glucose, galactose, xylose and arabinose or mixtures thereof. Glucose in anhydrous crystalline form is the most preferred.

3. Acid Catalyst

Acid catalysts include those selected from the group consisting of mineral acids like hydrochloric acid, sulfuric acid, phosphoric acid, phosphorous acid, toluene sulfonic acid, sulfonic acid, boron trifluoride, styrene sulfonic acid, alkyl sulfonic acids, alkyl-aryl sulfonic acids, naphthalene sulfonic acid and related materials, and acidic ion exchange resins containing sulfonic acid groups.

GENERAL PROCEDURE

To a one liter flask equipped with a mechanical stirrer, thermometer, dropping funnel, vacuum line and Dean Stark Trap is added the specified amount of the specified dimethicone copolyol and the specified amount of the specified saccharide source under good agitation. The resulting slurry is heated under a vacuum of 30 mm to a temperature of 57 C., at this temperature water begins to be removed. The reaction mass is heated to 110 C. at which time the 0.5% of the total weight of the batch of the specified acid catalyst is introduced through the dropping funnel. The reaction mixture is held at a temperature of between 100 C. and 120 C. for between 5 and 15 hours while the water is distilled off.

The resulting product is an amber oil which is neutralized using NaOH and used without additional purification.

EXAMPLES

| Example | Dimethicone Copolyol Example #/ | Grams | Saccharide Ex. #/ | Grams | Catalyst |
|---|---|---|---|---|---|
| 40 | 1 | 1,607.0 | 14 | 136.6 | HCl |
| 41 | 2 | 1,402.0 | 15 | 136.6 | $H_2SO_4$ |
| 42 | 3 | 3,339.0 | 16 | 136.6 | $H_3PO_4$ |
| 43 | 4 | 240.0 | 17 | 136.6 | $H_3PO_3$ |
| 44 | 5 | 3,044.2 | 18 | 136.6 | $BF_3$ |
| 45 | 6 | 1,920.3 | 19 | 136.6 | Toluene sulfonic acid |
| 46 | 7 | 2,450.8 | 20 | 136.6 | Styrene sulfonic acid |
| 47 | 8 | 1,043.3 | 21 | 136.6 | $H_2SO_4$ |
| 48 | 9 | 345.1 | 22 | 136.6 | HCl |
| 49 | 10 | 2,055.0 | 23 | 136.6 | $H_3PO_4$ |
| 50 | 11 | 3,450.0 | 24 | 136.6 | $H_2SO_4$ |
| 51 | 12 | 17,250.3 | 25 | 136.6 | $BF_3$ |
| 52 | 13 | 2,967.2 | 26 | 136.6 | HCl |
| 53 | 1 | 1,607.1 | 27 | 136.6 | $H_2SO_4$ |
| 54 | 2 | 1,402.0 | 28 | 136.6 | $H_3PO_4$ |
| 55 | 3 | 3,539.0 | 29 | 136.6 | HCl |
| 56 | 4 | 240.0 | 30 | 136.6 | $H_2SO_4$ |
| 57 | 5 | 3,040.8 | 31 | 136.6 | $H_2SO_4$ |
| 58 | 6 | 1,920.0 | 32 | 136.6 | HCl |
| 59 | 7 | 2,450.0 | 33 | 136.6 | $H_3PO_4$ |
| 60 | 8 | 1,043.3 | 34 | 136.6 | $BF_3$ |
| 61 | 9 | 345.0 | 35 | 136.6 | $H_2SO_4$ |
| 62 | 10 | 2,055.2 | 36 | 136.6 | $BF_3$ |
| 63 | 11 | 3,450.2 | 37 | 136.6 | HCl |
| 64 | 12 | 17,250.1 | 38 | 136.6 | $H_3PO_4$ |
| 65 | 13 | 2,967.0 | 39 | 136.6 | $H_2SO_4$ |

APPLICATIONS EVALUATIONS

Eye Irritation

Alkyl glycosides which are generally accepted as having lower irritation potential than fatty sulfates when evaluated in the Draize eye irritation test. The Draize Test measures eye irritation on a scale of 0 (none) to 110 (high). When tested at 12% active. Typically, sodium lauryl sulfate scores between 20 and 30 in such tests, alkyl glycosides score between 10 and 18 and the compounds of this invention generally score between 0 and 5. Consequently, the compounds of the present invention are classified as non-irritating compounds. The compounds of the present invention were also found to mitigate or reduce the irritation to the eye of sodium lauryl sulfate, this would suggest the potential of marketing blends of these materials as milder surface active agents,

Skin Irritation

Primary skin irritation index is defined on a scale of 0 to 8. When evaluated at 12% active sodium lauryl sulfate typically scores 6, alkyl glycosides 2.5 and the compounds of the present invention generally score below 0.5. The compounds of the present invention are very mild to the skin.

The compounds of the present invention are very mild surface active agents which are ideally suited for use in personal care compositions like hair and skin care products.

What is claimed is:

1. A silicone glycoside which is prepared by the reaction of
   (a) a dimethicone copolyol compound conforming to the following structure:

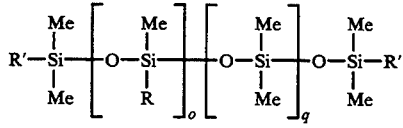

wherein:
   Me is methyl;
   R is $-(CH_2)_3-O-(EO)_a-(PO)_b-(EO)_c-H$;
   R' is selected from the group consisting of $CH_3$ and $-(CH_2)_3-O-(EO)_a-(PO)_b-(EO)_c-H$, with the proviso that
   R' cannot be $CH_3$ when o is zero;
   EO is $-(CH_2CH_2-O)-$;
   PO is a $-(CH_2CH(CH_3)-O)-$;
   a, b and c are independently integers ranging from 0 to 20;
   o is an integer ranging from 0 to 200; and
   q is an integer ranging from 0 to 1,100; with
   (b) a saccharide or saccharide source; and
   (c) an acid catalyst;
said reaction is carried out at temperature of between 100 C. and 120 C. for between 5 and 15 hours.

2. A silicone glycoside of claim 1 wherein the dimethicone copolyol compound conforms to the following structure:

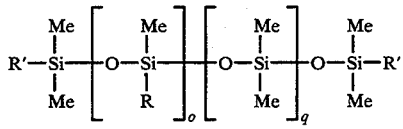

wherein:
  Me is methyl;
  R is —(CH$_2$)$_3$—O—(EO)$_a$—(PO)$_b$—(EO)$_c$—H;
  R' is —(CH$_2$)$_3$—O—(EO)$_a$—(PO)$_b$—(EO)$_c$—H;
  EO is —(CH$_2$CH$_2$—O)—;
  PO is a —(CH$_2$CH(CH$_3$)—O)—;
  a, b and c are independently integers ranging from 0 to 20;
  o is 0; and
  q is an integer ranging from 0 to 1,100.

3. A silicone glycoside of claim 1 wherein a, b and c are each zero.

4. A silicone glycoside of claim 1 wherein a, b and c are each greater than 0.

5. A silicone glycoside of claim I wherein the saccharide is glucose.

6. A silicone glycoside of claim I wherein the saccharide is starch.

7. A silicone glycoside of claim 1 wherein the saccharide is fructose.

8. A silicone glycoside of claim 1 wherein the saccharide is sucrose.

9. A silicone glycoside of claim 1 wherein the saccharide is lactose.

10. A silicone glycoside of claim 1 wherein the dimethicone copolyol compound conforms to the following structure:

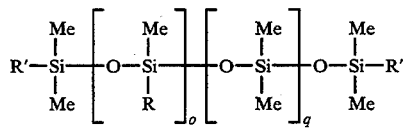

wherein:
  Me is methyl;
  R is —(CH$_2$)$_3$—O—(EO)$_a$—(PO)$_b$—(EO)$_c$—H;
  R' is CH$_3$;
  EO is —(CH$_2$CH$_2$—O)—;
  PO is a —(CH$_2$CH(CH$_3$)—O)—;
  a, b and c are independently integers ranging from 0 to 20;
  o is an integer ranging from 1 to 200; and
  q is an integer ranging from 0 to 1,100.

11. A silicone glycoside of claim 10 wherein a, b and c are each zero.

12. A silicone glycoside of claim 10 wherein a, b and c are each greater than 0.

13. A silicone glycoside of claim 10 wherein the saccharide is glucose.

14. A silicone glycoside of claim 10 wherein the saccharide is starch.

15. A silicone glycoside of claim 10 wherein the saccharide is fructose.

16. A silicone glycoside of claim 10 wherein the saccharide is sucrose.

17. A silicone glycoside of claim 10 wherein the saccharide is lactose.

18. A silicone glycoside of claim 10 wherein the saccharide is methyl glycoside.

19. A silicone glycoside of claim 10 wherein the saccharide is maltose.

20. A silicone glycoside of claim 10 wherein the saccharide is ribose.

* * * * *